(12) United States Patent
Nath et al.

(10) Patent No.: US 8,080,656 B2
(45) Date of Patent: Dec. 20, 2011

(54) PROCESS FOR THE PREPARATION OF APREPITANT

(75) Inventors: Asok Nath, Gurgaon (IN); Hiten Sharadchandra Mehta, Gurgaon (IN); Mohan Prasad, Gurgaon (IN)

(73) Assignee: Ranbaxy Laboratories Limited, New Delhi (IN)

( * ) Notice: Subject to any disclaimer, the term of this patent is extended or adjusted under 35 U.S.C. 154(b) by 404 days.

(21) Appl. No.: 12/089,297

(22) PCT Filed: Oct. 5, 2006

(86) PCT No.: PCT/IB2006/053649
§ 371 (c)(1),
(2), (4) Date: Jul. 30, 2009

(87) PCT Pub. No.: WO2007/039883
PCT Pub. Date: Apr. 12, 2007

(65) Prior Publication Data
US 2010/0004242 A1   Jan. 7, 2010

(30) Foreign Application Priority Data
Oct. 5, 2005   (IN) .......................... 2679/DEL/2005

(51) Int. Cl.
*C07D 413/02* (2006.01)
*C07D 295/00* (2006.01)
(52) U.S. Cl. ....................... 544/132; 544/171
(58) Field of Classification Search .................. 544/132, 544/171
See application file for complete search history.

(56) References Cited

U.S. PATENT DOCUMENTS

| | | | |
|---|---|---|---|
| 5,637,699 A | 6/1997 | Dorn et al. | 540/524 |
| 5,691,336 A | 11/1997 | Dorn et al. | 514/236.2 |
| 5,719,147 A | 2/1998 | Dorn et al. | 514/227.5 |
| 6,096,742 A | 8/2000 | Crocker et al. | 514/241 |
| 6,229,010 B1 | 5/2001 | Crocker et al. | 544/132 |

FOREIGN PATENT DOCUMENTS

| | | |
|---|---|---|
| WO | WO 95/18124 | 7/1995 |
| WO | WO 96/20009 | 7/1996 |
| WO | WO 99/01444 | 1/1999 |
| WO | WO 03/089429 | 10/2003 |

OTHER PUBLICATIONS

Hale et al., "Structural Optimization Affording 2-(R)-(1-(R)-3,5-Bis(trifluoromethyl)phenylethoxy)-3-(S)-(4-fluoro)phenyl-4-(3-oxo-1,2,4-triazol-5-yl)methylmorpholine, a Potent, Orally Active, Long-Acting Morpholine Acetal Human NK-1 Receptor Antagonist", *Journal of Medicinal Chemistry*, 41(23):4607-4614 (1998).

*Primary Examiner* — Rebecca Anderson
*Assistant Examiner* — Samantha Shterengarts

(57) ABSTRACT

The present invention relates to a highly pure (2R,3S)-4-benzyl-3-(4-fluorophenyl)morpholin-2-yl 3,5-bis(trifluoromethyl)benzoate of Formula II, and a process for its preparation. The present invention further provides a process for preparation of Aprepitant of Formula I or pharmaceutically acceptable salt thereof, using the highly pure compound of Formula II. The present invention also provides a process for preparation of Aprepitant of Formula I or pharmaceutically acceptable salt thereof which comprises of cyclising the compound of Formula VII at elevated temperature, in the absence of solvent.

1 Claim, 2 Drawing Sheets

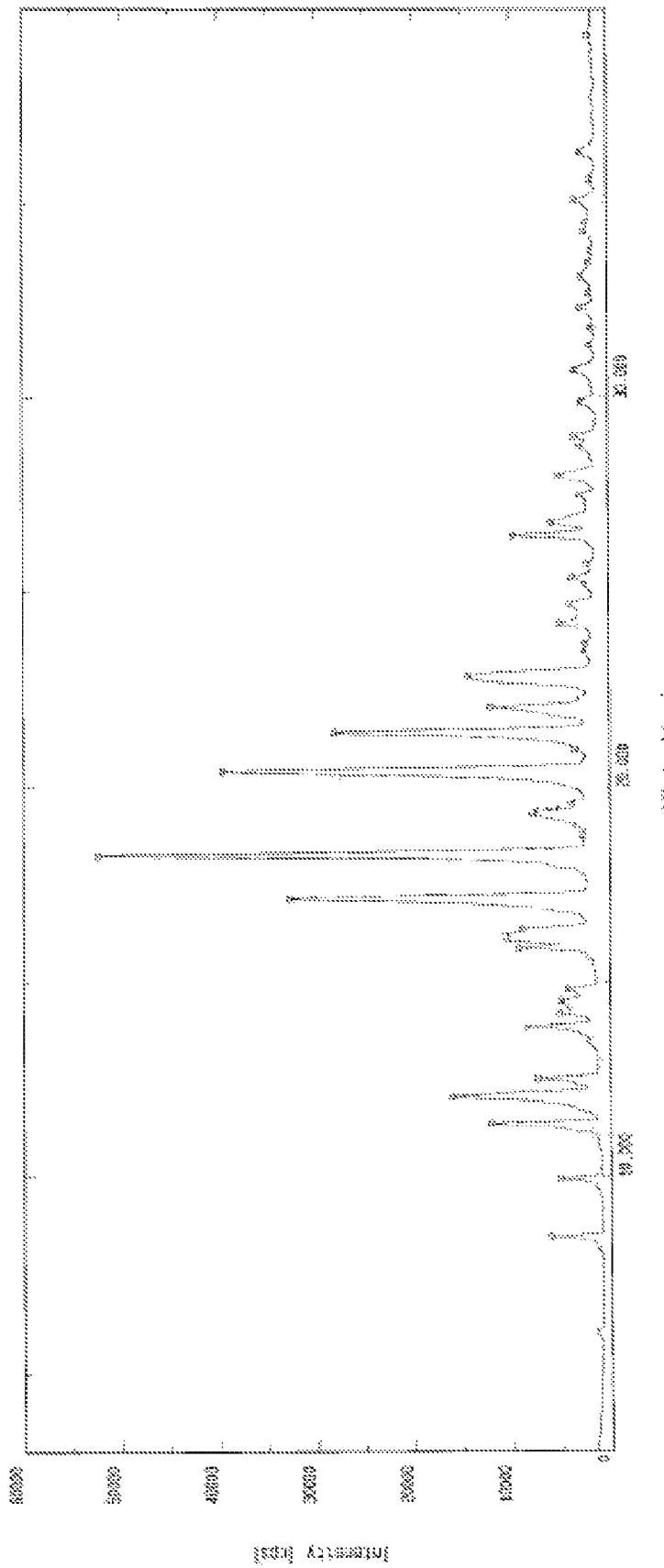
FIGURE 1: XRPD OF FORM A OF (2R,3S)-4-BENZYL-3-(4-FLUOROPHENYL)MORPHOLIN-2-YL 3,5-BIS(TRIFLUOROMETHYL)BENZOAT

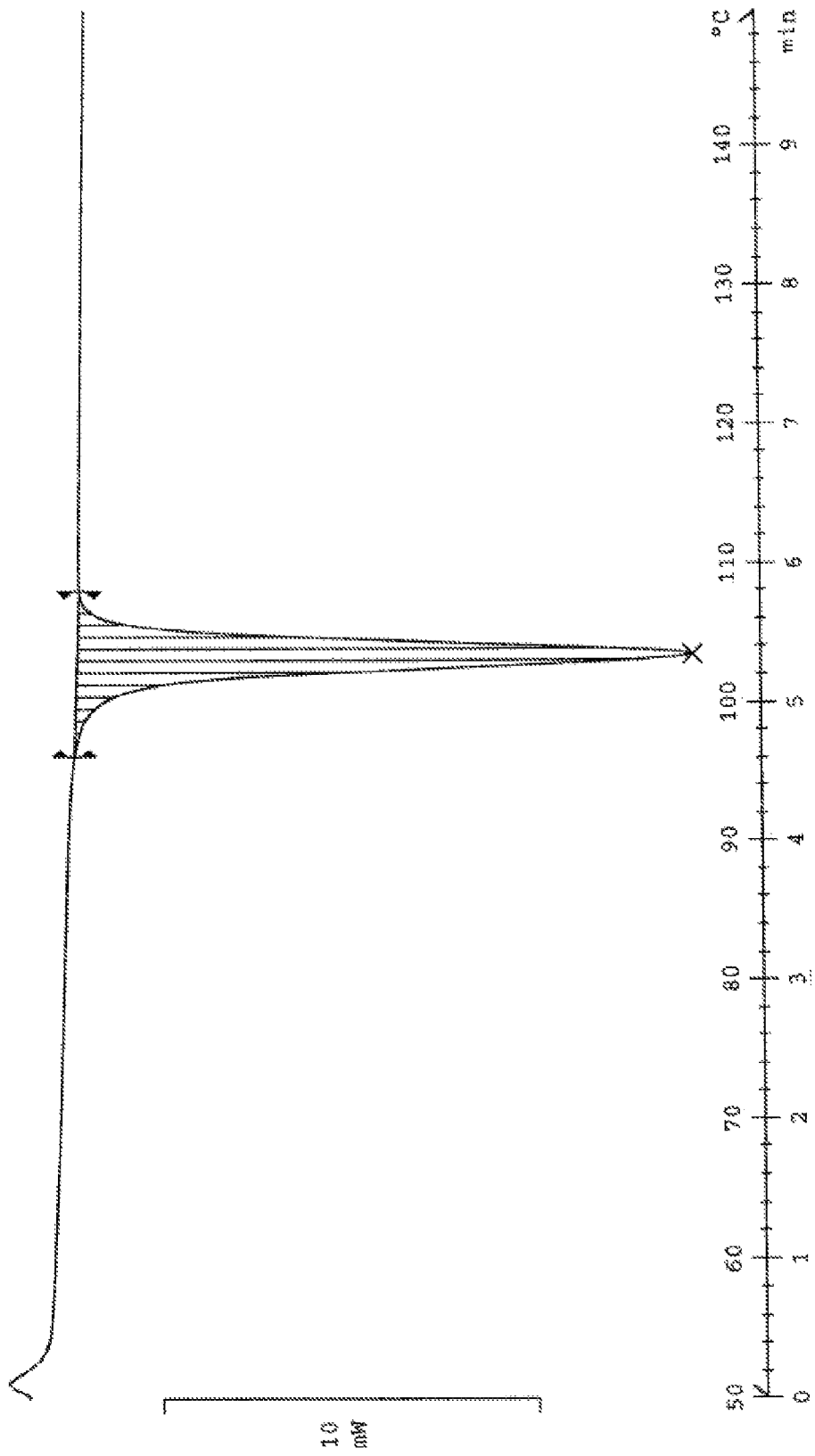

PROCESS FOR THE PREPARATION OF APREPITANT

FIELD OF THE INVENTION

The present invention relates to a highly pure (2R, 3S)-4-benzyl-3-(4-fluorophenyl)morpholin-2-yl 3,5-bis(trifluoromethyl)benzoate of Formula II, and a process for its preparation. The present invention further provides a process for preparation of Aprepitant of Formula I or pharmaceutically acceptable salt thereof, using the highly pure compound of Formula II. The present invention also provides a process for preparation of Aprepitant of Formula I or pharmaceutically acceptable salt thereof which comprises of cyclising the compound of Formula VII at elevated temperature, in the absence of solvent.

BACKGROUND OF THE INVENTION

Aprepitant of Formula I is a substance P/neurokinin 1 (NK1) receptor antagonist, chemically described as 5-[[(2R, 3S)-2-[(1R)-1-[3,5-bis(trifluoromethyl)phenyl]ethoxy]-3-(4-fluorophenyl)-4-morpholinyl]methyl]-1,2-dihydro-3H-1,2,4-triazol-3-one and in combination with other antiemetic agents, is indicated for the prevention of acute and delayed nausea and vomiting associated with initial and repeat courses of highly emetogenic cancer chemotherapy, including high-dose cisplatin.

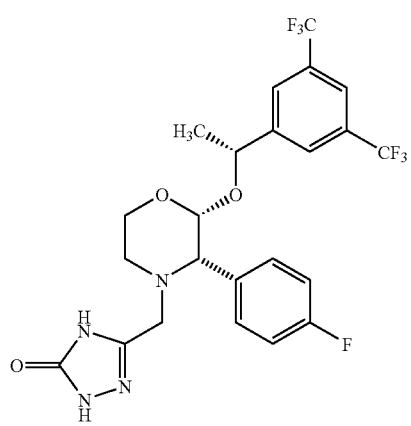

Formula I

The key intermediate (2R,3S)-4-benzyl-3-(4-fluorophenyl)morpholin-2-yl 3,5-bis(trifluoromethyl)benzoate of Formula II, is useful in the preparation of pharmaceutical compounds, which are substances P (or neuroklinin-1) receptor antagonists.

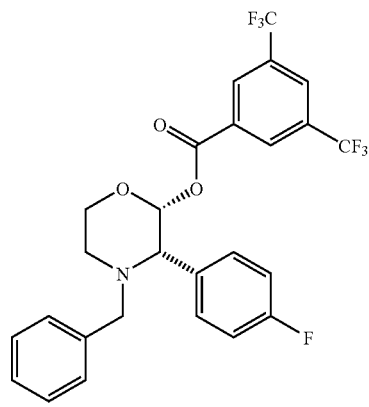

Formula II

U.S. Pat. No. 5,719,147 provides a process for the preparation of compound of Formula II, which involves reacting (3S)-4-benzyl-3-(4-fluorophenyl)morpholin-2-one, the compound of Formula III,

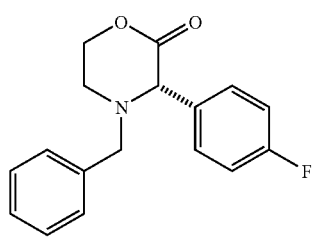

Formula III with L-selectride, and treating the reaction mixture with 3,5-bis(trifluoromethyl) benzoyl chloride, the compound of Formula IV,

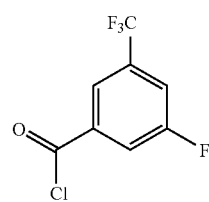

Formula IV isolating the crude product using flash chromatography on silica gel using hexane/ether.

U.S. Pat. Nos. 6,096,742 and 6,229,010 provide a process for the preparation of compound of Formula II, wherein the process involves isolating the product as a hydrochloride salt by treating with hydrochloric acid in diethyl ether, which is then converted into freebase by reacting it with toluene and aqueous sodium bicarbonate.

J. Med. Chem., 1998, 41, 4607-4614, provides a process for the preparation of compound of Formula II wherein the process involves isolating the crude product using flash chromatography on silica gel and then crystallizing from isopropyl alcohol.

Another key intermediate of Formula VII is also useful in the preparation of pharmaceutical compounds, which are substances P (or neuroklinin-1) receptor antagonists.

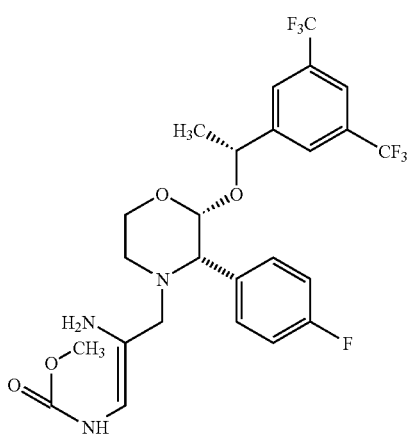

Formula VII

U.S. Pat. Nos. 5,719,147 and 5,637,699 provides a process for the preparation of compound of Formula I, which involves dissolving the compound of formula VII in xylene and heating to 137° C. to obtain aprepitant.

U.S. Pat. Nos. 6,096,742 and 6,229,010 provides a process for the preparation of compound of Formula I, which involves dissolving the compound of formula VII in xylene and diisopropylethylamine and heating to 135° C. to obtain aprepitant.

PCT Application No. WO 03/089429 provide a process for the preparation of compound of Formula I, which involves partially concentrating the organic layer containing the compound of formula VII and toluene at atmospheric pressure, heating the resulting solution in toluene to 140-150° C. to obtain aprepitant.

SUMMARY OF THE INVENTION

The present inventors have found a process for preparation of (2R,3S)-4-benzyl-3-(4-fluorophenyl)morpholin-2-yl 3,5-bis(trifluoromethyl)benzoate, of Formula II, which is characterized by yields and purity that are superior to those of the processes known in the art.

The present inventors have also found a process for preparation of the compound of formula I which involves cyclising the compound of Formula VII at elevated temperature, in the absence of solvent.

DETAILED DESCRIPTION OF THE INVENTION

A first aspect of the present invention provides a process for the preparation of highly pure (2R,3S)-4-benzyl-3-(4-fluorophenyl)morpholin-2-yl 3,5-bis (trifluoromethyl)benzoate, of Formula II, which comprises of,
a) treating compound of Formula III or its salt thereof, with L-Selectride,

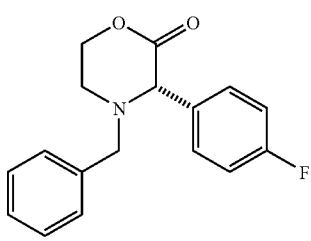

Formula III b) reacting the mixture of step a) with the compound of Formula IV,

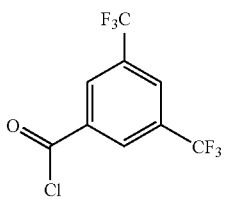

Formula IV to obtain compound of Formula II,
c) crystallising the compound of Formula II from an organic solvent,
d) isolating the highly pure compound of Formula II from the reaction mass thereof.

The starting material (S)-3-(4-fluorophenyl)-4-(phenylmethyl)-2-morpholinone or its salt used is prepared by any of the methods known in the literature. (3S)-4-benzyl-3-(4-fluorophenyl)morpholin-2-one hydrochloride or its freebase, of compound of Formula III, is dissolved in an organic solvent and cooled to about −50° C. to −100° C. L-Selectride (Lithium tri-sec-butylborohydride) is added maintaining the temperature at about −50° C. to −100° C. Then 3,5-bis(tirfluoromethyl)benzoyl chloride, is added at the same temperature. The reaction is quenched with an acid and the temperature of the reaction mixture is raised to room temperature. The solution is concentrated under reduced pressure and the residue obtained is dissolved in water and hexane. The organic layer is separated and washed with sodium carbonate and water. The organic layer is recovered under vacuum and the residue is flushed with an organic solvent. The residue was dissolved in an organic solvent at about 50° C., cooled to 0° C. and stirred at about 0 to 5° C. for about 1 hour to complete crystallization. The solid obtained is filtered and washed with an organic solvent. The wet solid was slurried in an organic solvent at about 45° C. and cooled to about 5° C. The slurry is stirred, filtered and the wet solid is washed with an organic solvent and dried.

The organic solvent used can be selected from a group comprising of alcohols, ketones, polar aprotic solvents, esters or mixtures thereof. The organic solvent comprises of methanol, ethanol, n-propanol, isopropanol, n-butanol, isobutanol, tert-butanol, acetone, ethyl methyl ketone, tetrahydrofuran, N,N-dimethylacetamide, N,N-dimethylformamide, acetonitrile, 1,4-dioxane, N-methylpyrrolidone, ethyl acetate or mixtures thereof.

The acid used can be organic acid selected from group comprising of formic acid, acetic acid, propionic acid, anhydrides of carboxylic acids, methanesulphonic acid and the like.

A second aspect of the invention provides highly pure (2R,3S)-4-benzyl-3-(4-fluorophenyl)morpholin-2-yl 3,5-bis (trifluoromethyl)benzoate, compound of Formula II, having a HPLC purity of above 99%.

A third aspect of the invention provides highly pure (2R,3S)-4-benzyl-3-(4-fluorophenyl)morpholin-2-yl 3,5-bis(trifluoromethyl)benzoate, compound of Formula II, having a HPLC purity of above 99.5%.

A fourth aspect of the invention provides highly pure (2R,3S)-4-benzyl-3-(4-fluorophenyl)morpholin-2-yl 3,5-bis(trifluoromethyl)benzoate, compound of Formula II, having a HPLC purity of above 99.9%.

A fifth aspect of the present invention provides polymorphic Form A of (2R,3S)-4-benzyl-3-(4-fluorophenyl)morpholin-2-yl 3,5-bis(trifluoromethyl)benzoate, compound of Formula II, having X-Ray Powder Diffraction (XRPD) pattern as depicted in FIG. 1 of the accompanied drawing wherein characteristic 2δ values are obtained at 8.46, 9.96, 11.36, 12.06, 12.52, 13.86, 14.20, 14.52, 15.86, 16.16, 16.34, 17.14, 18.24, 19.30, 20.40, 21.40, 22.06, 22.86, 24.20, 24.70, 26.46, 26.78, 28.00. The polymorphic Form A of (2R,3S)-4-benzyl-3-(4-fluorophenyl)morpholin-2-yl 3,5-bis(trifluoromethyl)benzoate has characteristic Differential Scanning Calorimetric (DSC) thermogram as depicted in FIG. 2 of the accompanied drawing wherein the characteristic endothermic absorptions are observed between 96-108° C.

A sixth aspect of the invention provides a process for the preparation of Aprepitant of Formula I or salt thereof wherein the said process comprises of, a) treating compound of Formula III, with L-Selectride,

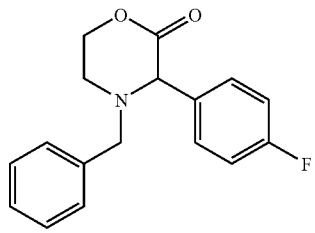

Formula III b) reacting the mixture of step a) with the compound of Formula IV,

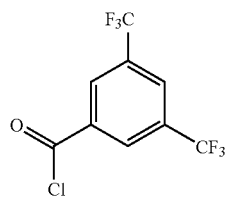

Formula IV to get a compound of formula II, c) crystallizing the compound of Formula II from an organic solvent, d) isolating the highly pure compound of Formula II from the reaction mass thereof, e) reacting the highly pure compound of Formula II with dimethyl titanocene to obtain a compound of Formula V,

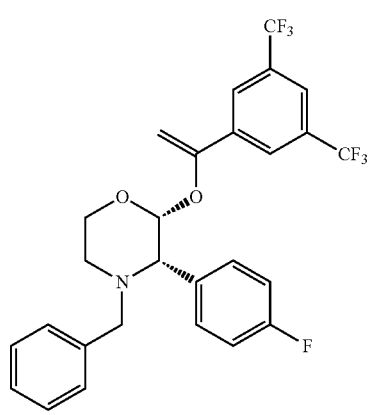

Formula V f) hydrogenating the compound of Formula V to obtain a compound of Formula VI or acid addition salt thereof,

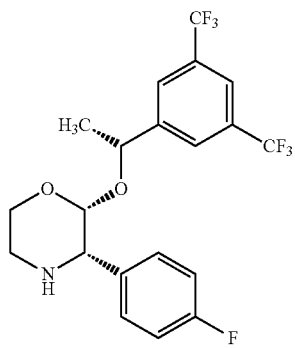

Formula VI g) reacting the compound of Formula VI or acid addition salt there of with N-methylcarboxyl-2-chloroacetamidrazone to obtain a compound of Formula VII,

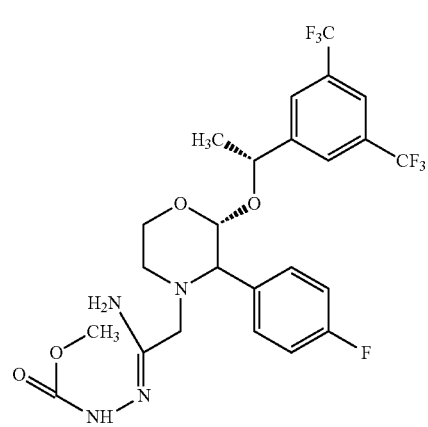

Formula VII h) cyclising the compound of Formula VII, to obtain Aprepitant for Formula I.

A seventh aspect of the present invention provides a process for preparation of Aprepitant of Formula I or salt thereof, which comprises of,

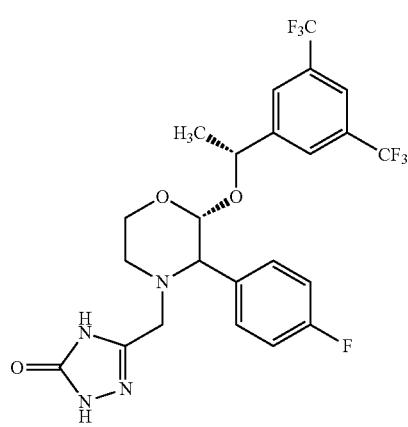

Formula I cyclising the compound of Formula VII,

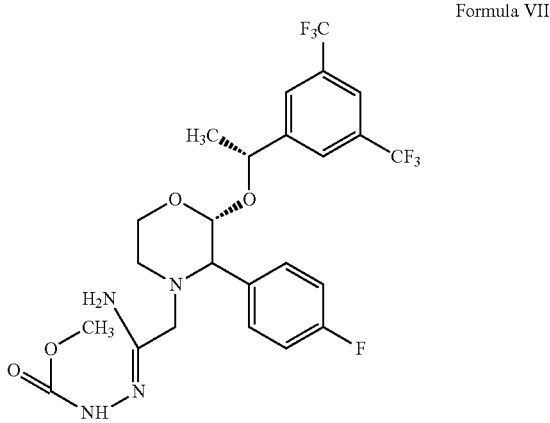

Formula VII at elevated temperature, in the absence of solvent.

The highly pure compound of Formula II prepared as per the first aspect of the invention is added to a solution of dimethyl titanocene. The reaction mixture is heated to about 80° C. and stirred for 4-8 hours in dark. The mixture is concentrated under reduced pressure. n-Heptane is added and the resulting slurry is filtered and washed. The combined filtrate is concentrated under reduced pressure. Sodium carbonate, methanol and water are added to the residual liquid and the resulting mixture is stirred at about 40-45° C., cooled to about 25° C., filtered and washed twice with an organic solvent. The combined filtrate is concentrated under reduced pressure. To the residue an organic solvent is added and heated. The mixture is cooled to about room temperature and water in an organic solvent is added. The resulting slurry is filtered, washed and dried to get the compound of Formula V.

Compound of Formula V in an organic solvent or mixtures thereof is mixed with a hydrogenating agent. The mixture is hydrogenated under pressure of about 35-55 psi for 1 to 10 hours. After completion of reaction, the reaction mixture is filtered and combined filtrate is concentrated under reduced pressure. The residue is dissolved in an organic solvent and treated with activated carbon. The slurry is filtered and washed twice with an organic solvent and the combined filtrate is concentrated under reduced pressure. The residue dissolved in an organic solvent is added with an acid in an organic solvent in over about 15 minutes. Hexane is added and the resulting slurry is stirred at room temperature for about 2-4 hours. The solid is filtered, washed and dried to get the acid addition salt the compound of Formula VI.

The acid addition salt the compound of Formula VI is purified by treating the crude acid addition salt with a mixture of aqueous sodium carbonate solution. The organic layer is washed with water and concentrated under reduced pressure. The residue dissolved in an organic solvent is added to a solution of an acid in an organic solvent in over 15 minutes. Hexane is added and the resulting slurry is stirred at room temperature for about 2 hours. The solid is filtered, washed and dried to get the pure acid addition salt the compound of Formula VI.

To a stirred mixture of compound of Formula VI or its acid addition salt thereof, an inorganic base in organic solvent is added a solution of N-methylcarboxyl-2-chloroacetamidrazone in an organic solvent at about 15-30° C. After stirring the reaction mixture at the same temperature for about 1 hour, the reaction mixture is quenched with water and extracted with an organic solvent. The organic layer is washed twice with water and concentrated at atmospheric pressure to maximum extent. The viscous liquid residue is heated at elevated temperature for about 2 hours to get the solid residue. After completion of reaction, an organic solvent is added and the slurry is cooled to room temperature filtered and washed with an organic solvent. The wet solid is dissolved in an organic solvent and treated with activated carbon for about 1 hour, filtered and washed. The combined filtrate is cooled to about 25° C. and water is added. The slurry is stirred at about 25-30° C. for about 1 hour and filtered. The wet solid is washed and dried.

The 'organic solvent' used are known to a person of ordinary skills in art through several literature references.

The 'hydrogenating agent' used is selected from group comprising of noble metals such as palladium on carbon, palladium acetate, palladium chloride, platinum oxide, platinum chloride, ruthenium and rhodium.

The term "acid addition salt" of compound of Formula VI comprise of inorganic acid addition salts and organic acid addition salts. The inorganic acid addition salts are hydrochloride, hydrobromide, sulphate, nitrate, phosphate and the like. The organic acid addition salts are acetate, maleate, succinate, valinate, glycinate, glutarate, aspartate, arginate, mesylate, tosylate and the like.

The 'acid addition salt' is defined as above and for the preparation the corresponding inorganic acid or organic acid can be used.

The inorganic base can be selected from the group comprising of alkali and alkaline earth metal hydroxide or alkoxide or carbonate or bicarbonate and the like.

The term "elevated temperature" is selected in the range of about 100-180° C.

An eighth aspect of the invention provides a highly pure Aprepitant of Formula I having HPLC purity of 99.5% and above.

A ninth aspect of the invention provides a pharmaceutical composition comprising highly pure Aprepitant of Formula I having a HPLC purity of 99.5% and above along with pharmaceutically acceptable carrier/excipient.

A tenth aspect of the invention provides a method of preventing acute and delayed nausea and vomiting associated with initial and repeat courses of highly emetogenic cancer chemotherapy, including high-dose cisplatin either alone or in combination with other antiemetic agents, which comprises administering to the patient in need of such treatment a therapeutically effective amount of highly pure Aprepitant of Formula I having a HPLC purity of 99.5% and above.

The term "highly pure (2R,3S)-4-benzyl-3-(4-fluorophenyl)morpholin-2-yl 3,5-bis(trifluoromethyl)benzoate, of Formula II" in context to present invention relates to (2R,3S)-4-benzyl-3-(4-fluorophenyl)morpholin-2-yl 3,5-bis(trifluoromethyl) benzoate, of Formula II, or pharmaceutically acceptable salt thereof having purity more than 99% as measured by HPLC method.

The term "highly pure Aprepitant of Formula I" in context to present invention relates to highly pure Aprepitant of Formula I, or pharmaceutically acceptable salt thereof having purity more than 99.5% as measured by sensitive HPLC method.

BRIEF DESCRIPTION OF THE DRAWINGS

FIG. 1 depicts XRPD of polymorphic Form A of (2R,3S)-4-benzyl-3-(4-fluorophenyl)morpholin-2-yl 3,5-bis(trifluoromethyl)benzoate, the compound of Formula II.

FIG. 2 depicts DSC of polymorphic Form A of (2R,3S)-4-benzyl-3-(4-fluorophenyl)morpholin-2-yl 3,5-bis(trifluoromethyl)benzoate, the compound of Formula II.

Powder XRD of the samples were determined by using X-Ray Difractometer, Rigaku Corporation, RU-H3R, Goniometer CN2155A3, X-Ray tube with Cu target anode, Divergence slits 10, Receiving slit 0.15 mm, Scatter slit 1°, Power: 40 KV, 100 mA, Scanning speed: 2 deg/min step: 0.02 deg, Wave length: 1.5406 A While the present invention has been described in terms of its specific embodiments, certain modifications and equivalents will be apparent to those skilled in the art and are intended to be included within the scope of the present invention.

EXAMPLE 1

Preparation of (2r,3s)-4-Benzyl-3-(4-Fluorophenyl) Morpholin-2-Yl 3,5-Bis(Trifluoromethyl)Benzoate (S)-3-(4-fluorophenyl)-4-(phenylmethyl)-2-morpholinone hydrochloride (100 g) was added to a stirred mixture of sodium carbonate (50 g), water (500 ml) and ethyl acetate (500 ml). The resulting mixture was washed twice with water (300 ml). The organic solution was concentrated under reduced pressure and flushed with tetrahydrofuran (200 ml). The resulting free base residue was dissolved in tetrahydrofuran (800 ml) and cooled to −75° C. L-Selectride (Lithium tri-sec-butylborohydride) (280 g, 1M solution in tetrahydrofuran) was added maintaining the temperature at −75° C. to −70° C. The reaction mixture was stirred at the same temperature for 30 minutes and then 3,5-bis(tirfluoromethyl)benzoyl chloride (112 g) was added slowly maintaining the temperature at −75° C. to −70° C. The reaction was quenched with acetic acid (10 ml) in tetrahydrofuran (40 ml) and the temperature of the reaction mixture was raised to room temperature. The solution was concentrated under reduced pressure and the residue so obtained was dissolved in water (500 ml) and hexane (500 ml). The organic layer was separated and washed twice with 10% aqueous sodium carbonate (250 ml) and water (250 ml). The organic layer was concentrated under reduced pressure and the residue was flushed with isopropyl alcohol (500 ml). The residue was dissolved in isopropyl alcohol (200 ml) at 50° C. The solution was slowly cooled to 0° C. and stirred at 0-5° C. for 1 hour. The solid obtained was filtered and washed with isopropyl alcohol (20 ml). The wet solid was slurried in isopropyl alcohol (100 ml) at 45° C. and cooled to 5° C. The slurry was stirred at 5-10° C. for 1 hour and filtered. The wet solid was washed twice with isopropyl alcohol (50 ml) and dried at 45° C. to get the title compound. Yield: 112 g. Melting point: 102-103° C. HPLC purity: 99.94%.

EXAMPLE 2

Preparation of (2r,3s)-4-Benzyl-2-({1-[3,5-Bis(Trifluoromethyl)Phenyl]Vinyl}Oxy)-3-(4-Fluorophenyl) Morpholine (2R,3S)-4-benzyl-3-(4-fluorophenyl)morpholin-2-yl 3,5-bis(trifluoromethyl) benzoate (80 g) was added to a solution of dimethyl titanocene (400 g, 20% solution in toluene). The reaction mixture was heated to about 80° C. and stirred at 80-83° C. for 5-6 hours in dark. After the completion of the reaction, the mixture was concentrated under reduced pressure up to an approximate volume of 300 ml. n-Heptane (240 ml) was added over 15 minutes and the slurry was filtered, washed twice with n-heptane (80 ml). The combined filtrate was concentrated under reduced pressure up to an approximate volume of 300 ml. Sodium carbonate (14 g), methanol (240 ml) and water (12 ml) were added to the residual liquid and the resulting mixture was stirred at 40-45° C. for 12 hours, cooled to 25° C., filtered and washed twice with toluene (160 ml). The combined filtrate was concentrated under reduced pressure up to the maximum extent. The residue was dissolved in methanol (160 ml) and again concentrated under reduced pressure. Methanol (400 ml) was added to the residue and heated to 50° C. The mixture was cooled to 25° C. and 50% (v/v) water in methanol was added over 1.5 hours. The resulting slurry was filtered, washed twice with 20% (v/v) water in methanol (80 ml) and dried at 45-50° C. to get the title compound. Yield: 72 g. HPLC purity: 99.9%

EXAMPLE 3

Preparation of (2r,3s)-2-{(1r)-1-[3,5-Bis(Trifluoromethyl)Phenyl]Ethoxy}-3-(4-Fluorophenyl)Morpholine 4-Methylbenzenesulfonate A solution of (2R,3 S)-4-benzyl-2-({1-[3,5-bis(trifluoromethyl)phenyl]vinyl}oxy)-3-(4-fluorophenyl)morpholine (50 g) in 1:1 ethyl acetate : absolute alcohol (500 ml) was mixed with 10% Pd—C (7.5 g) and the resulting mixture was hydrogenated with hydrogen at 40-45 psi pressure for 6-8 hours. After completion of reaction, the reaction mixture was filtered and the catalyst was washed twice with ethyl acetate (50 ml). The combined filtrate was concentrated under reduced pressure. The residue was dissolved in methyl tert-.butyl ether (150 ml) and treated with activated carbon (10 g). The slurry was filtered and washed twice with methyl tert.butyl ether (50 ml). The combined filtrate was concentrated under reduced pressure. The residue was dissolved in methyl tert.butyl ether (75 ml) and a solution of p-toluene sulphonic acid monohydrate (16.3 g) in methyl tert.butyl ether (75 ml) was added in slowly over 15 minutes. Hexane (450 ml) was added and the resulting slurry was stirred at room temperature for 2 hours. The solid was filtered, washed twice with 1:3 mixture of methyl tert.butyl ether: hexanes (50 ml) and dried at 50° C. to get the title compound. Yield: 37 g.

EXAMPLE 4

Preparation of Pure (2r,3s)-2-{(1r)-1-[3,5-Bis(Trifluoromethyl)Phenyl]Ethoxy}-3-(4-Fluorophenyl) Morpholine 4-Methylbenzenesulphonate (2R,3S)-2-{(1R)-1-[3,5-bis(trifluoromethyl)phenyl]ethoxy}-3-(4-fluorophenyl) morpholine 4-methylbenzenesulfonate (50 g) (crude) was treated with a mixture of 10% aqueous sodium carbonate solution (250 ml). The layers were separated and the organic layer was washed twice with water (125 ml). The organic layer was concentrated under reduced pressure. The residue was dissolved in methyl tert.butyl ether (75 ml) and a solution of p-toluene sulphonic acid monohydrate (14.8 g) in methyl tert.butyl ether (75 ml) was added in slowly over 15 minutes. Hexane (450 ml) was slowly added over 1 hour and the resulting slurry was stirred at room temperature for 2 hours. The solid was filtered, washed twice with 1:3 mixture of methyl tert.butyl ether:hexanes (50 ml) and dried at 50° C. to get the title compound. Yield: 45 g. HPLC purity: 99.9%

EXAMPLE 5

Preparation of 5-[[(2r,3s)-2-[(1r)-1-[3,5-Bis(Trifluoromethyl)Phenyl]Ethoxy]-3-(4-Fluorophenyl)-4-Morpholinyl]Methyl]-1,2-Dihydro-3h-1,2,4-Triazol-3-One (Aprepitant)

To a stirred mixture of (2R,3S)-2-{(1R)-1-[3,5-bis(trifluoromethyl)phenyl]ethoxy}-3-(4-fluorophenyl) morpholine 4-methylbenzenesulphonate (10 g), powdered potassium carbonate (8 g) in dimethyl sulfoxide (40 ml) was added a solution of N-methylcarboxyl-2-chloroacetamidrazone (2.9 g) in dimethyl sulfoxide (40 ml) at 20-23° C. over 20-30 minutes. After stirring the reaction mixture at the same temperature for 1 hour, the reaction mixture was quenched with water (80 ml) and extracted with toluene (100 ml). The organic layer was washed twice with water (50 ml) and concentrated at atmospheric pressure upto maximum extent. The viscous liquid residue was heated at 135-137° C. for 2 hours to get the solid residue. After completion of reaction, toluene (50 ml) was added and the slurry was cooled to room temperature. Then it was filtered, washed with toluene (20 ml). The wet solid was dissolved in methanol (70 ml) at 50° C. and treated with activated carbon (1 g) at 60-62° C. for 1 hour, filtered and washed with methanol (30 ml). The combined filtrate was cooled to 25° C. and water (50 ml) was added slowly over I hour. The slurry was stirred at 25-30° C. for 1 hour and filtered. The wet solid was washed with 2:1 mixture of methanol:water (30 ml) and dried at 50° C. under reduced pressure to get the title compound. Yield: 6 g HPLC purity:99.8%

The invention claimed is:

1. A process for the preparation of Aprepitant of Formula I

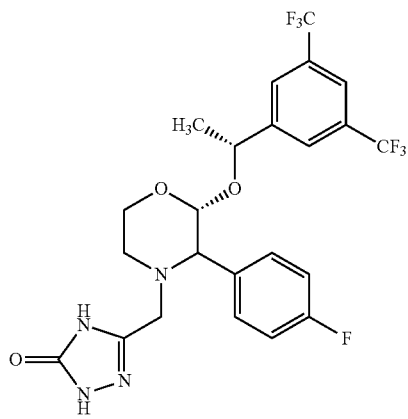

Formula I or a salt thereof, wherein said process comprises:
a) treating a compound of Formula III, with L-Selectride,

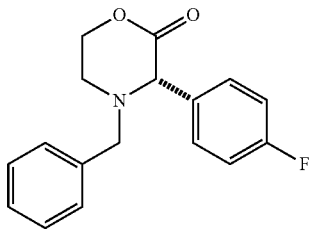

Formula III b) reacting the mixture of step a) with the compound of Formula IV,

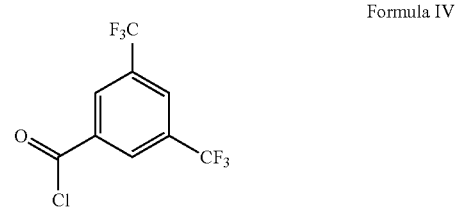

Formula IV to obtain a compound of Formula II,

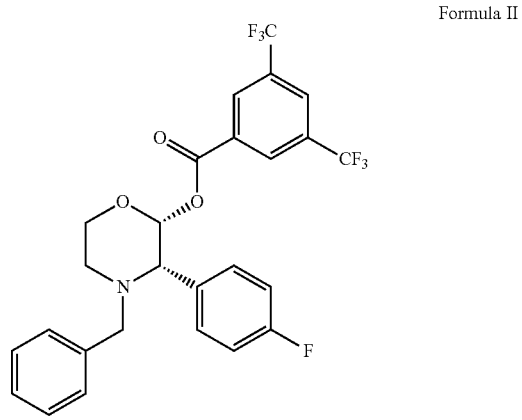

Formula II c) crystallizing the compound of Formula II from an organic solvent,
d) isolating a highly pure compound of Formula II from the reaction mass thereof,
e) reacting the highly pure compound of Formula II with dimethyl titanocene to obtain a compound of Formula V,

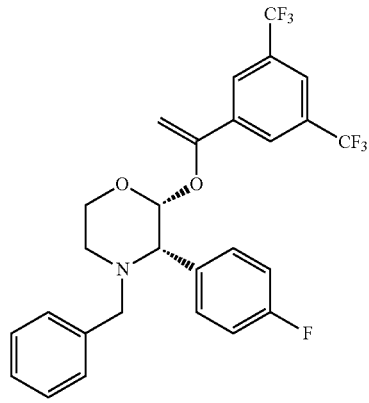

Formula V f) hydrogenating the compound of Formula V to obtain a compound of Formula VI,
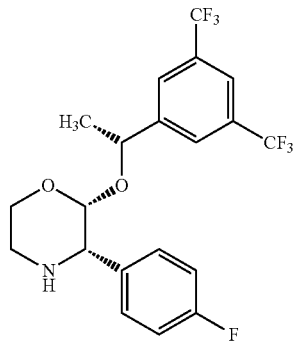
Formula VI
g) reacting the compound of Formula VI or an acid addition salt thereof with N-methylcarboxy-2-chloroacetamidrazone, to obtain a compound of Formula VII,
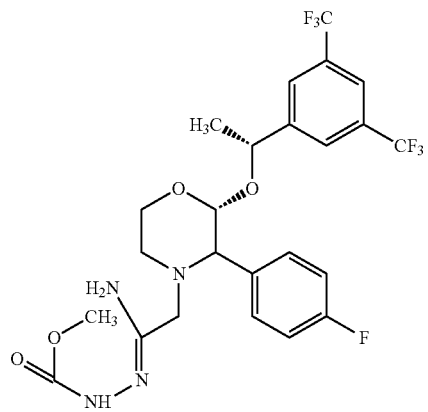
Formula VII
h) cyclising the compound of Formula VII, to obtain Aprepitant of Formula I.
* * * * *